United States Patent [19]
Brucker et al.

[11] Patent Number: 6,103,218
[45] Date of Patent: Aug. 15, 2000

[54] THERAPEUTIC NASAL SPRAY ADMINISTERED COMPOSITION CONTAINING FEVERFEW

[76] Inventors: Donald Brucker, 7777 Fay Ave., Suite 160, La Jolla, Calif. 92037; Lee H. Lorenzen, 15550-D Rockland Blvd., Irvine, Calif. 92718

[21] Appl. No.: 08/839,150

[22] Filed: Apr. 23, 1997

[51] Int. Cl.$^7$ ........................................................ A61K 9/12
[52] U.S. Cl. .......................... 424/45; 424/195.1; 514/944; 514/938
[58] Field of Search ................................... 424/45, 195.1; 514/944, 938

[56] References Cited

PUBLICATIONS

Vukovic, L. (1998). Natural Health, vol. 27, No. 5, p 121–125.
Bremness (ed.), Herbs (1990), pp. 91, 183, 185–186 and 201 Reader's Digest Assoc. Inc.
The Burton Goldberg Group (eds.), Alternative Medicine, The Definitive Guide (1995), pp. 264 and 266 Future Medicine Publishing Co.
Castleman, The Healing Herbs (1991), pp. 173–176 and 201–204, Rodale Press.
Garland, The Complete Book Of Herbs & Spices, (Reader's Digest: 1993), pp. 66, 106 and 275.
Tierra, The Herbs Of Life: Health & Healing Using Western & Chinese Techniques (1992), pp. 63 and 66–67, The Crossing Press.
"Herbal Roulette", Consumer Reports (Nov., 1995), pp. 698 and 701.

*Primary Examiner*—Thurman K. Page
*Assistant Examiner*—R. Bawa
*Attorney, Agent, or Firm*—Brown Martin Haller & McClain LLP

[57] ABSTRACT

A composition and delivery system are disclosed that will allow feverfew to be administered to a person in form in which an active ingredient of feverfew, particularly parthenolide can be readily and quickly assimilated by the person's body, particularly the central nervous system, and the therapeutic effects of the feverfew be rapidly imparted to the person. Feverfew is administered in the form of aqueous nasal spray composition, to provide therapeutic moisturization of nasal mucous membranes, relief of migraine headaches and antispasmodic effect, such as to relieve menstrual cramping or aid digestion. The effect is enhanced when the composition also contains nanoclustered resonant water. Vitamins, vitamin derivatives, surfactants, wetting agents, preservatives and emulsifiers may also be present.

39 Claims, No Drawings

THERAPEUTIC NASAL SPRAY ADMINISTERED COMPOSITION CONTAINING FEVERFEW

BACKGROUND OF THE INVENTION

1. Field of the Invention

The invention herein relates to therapeutic medications. More particularly it relates to therapeutic nasal sprays.

2. Description of the Prior Art

Feverfew (*Tanacetum parthenium*) is an herb in the Compositae family which has long been known to have therapeutic properties; see Bremness, (ed.), HERBS (1990), pp. 91, 185–186 and Castleman, THE HEALING HERBS (1991), pp. 173–176. At various times feverfew has been considered to have therapeutic properties for reducing high blood pressure, acting as a digestive tract antispasmodic, relieving menstrual cramps and, most importantly, relieving migraine headaches. It has been administered as the raw feverfew leaf, either fresh or frozen, which is taken by chewing or by swallowing pills or capsules in which the feverfew is incorporated. It has also been administered as a tea with a concentration of 0.5–1 teaspoonfuls of feverfew per cup of boiling water, and which is drunk after the tea has steeped for 5–10 minutes.

Such delivery systems have had significant problems. Raw feverfew leaves are bitter and therefore unpleasant to chew and the tea is unpleasant to drink. It has also been documented that raw feverfew leaves can cause oral ulcers or other irritation to the buccal membranes or mucous lining of the mouth. Therefore, when leaves are to be chewed, it has been recommended that they be chewed in combination with a larger quantity of an innocuous foodstuff, commonly slices of bread. The general use of feverfew in the form of capsules or pills has been an attempt to avoid the buccal irritation and ulcers and the bitter taste of the herb.

Administration of feverfew by swallowing of the chewed material, drinking of tea, or swallowing of capsules and pills means that the feverfew [and its apparent active ingredient, parthenolide; see The Burton Goldberg Group, (eds.), ALTERNATIVE MEDICINE; THE DEFINITIVE GUIDE (1995), p. 264] must be released and dispersed to the central nervous system or other affected organs through the gastrointestinal system. Such administration is slow and relatively inefficient. Consequently, the therapeutic effects of feverfew will not be quickly available to the person to whom the herb has been administered. This has been particularly significant in the treatment of migraine headaches. The severe effects of migraine headache on a person have been extensively and frequently documented, and delayed relief unnecessarily extends the period of the sufferer's discomfort.

Nasal sprays have heretofore been commercially available for moisturization of the nasal membranes. Such sprays normally are water containing surfactants to spread the water over the nasal membranes and enhance the penetration of the water into the surface layers of the membranes. There is no therapeutic function of the water penetration.

Nasal sprays or drops have also been known for relief of migraine headache, using conventional chemicals. For instance, nasal sprays or drops containing dihydroergotamine, sumatriptan succinate or lidocaine have variously been reported, used commercially or used investigationally.

Clustered water (or nanocluster resonant water) is the name given to water molecules associated in a unique physical structure. Various embodiments of clustered water have been identified in recent years. They can be artificially produced by subjecting quantities of water to strong magnetic fields; see, for instance, Lorenzen, NANOCLUSTERED SOLUTIONS AS A SUPPORT BASE TO OPTIMIZE COHERENT CELLULAR COMMUNICATION (1995). Clustered water samples have been shown by NMR spectroscopy and other types of analyses to have different freezing points, pH levels, surface tensions and electrical conductivity values than conventional distilled tap or colloidal water. In cellular organic systems it is believed that the presence of clustered water will alter cellular resonance and influence internal chemical and enzymatic reactions. The water clusters can be directed to bind to pharmacological active substances and thus enhance the pharmacological activity of such substances in cells.

SUMMARY OF THE INVENTION

There is a significant need for a delivery system that will allow feverfew to be administered to a person in a form in which an active ingredient of feverfew can be readily and quickly assimilated by the person's body, particularly the central nervous system, and the therapeutic effects of the feverfew be rapidly imparted to the person. Further, enhancement of the therapeutic effects of feverfew by a synergistic agent will permit lower dosages of feverfew to be effective therapeutic agents while reducing the incidence of undesirable side effects such as buccal membrane irritation or ulceration. These therapeutic effects are of particular benefit to sufferers of migraine headaches. In addition, feverfew provides significant antispasmodic effect, which can benefit a wide range of users, from women with the discomfort of menstrual cramping to those persons suffering digestive disorders involving intestinal spasms. With the compositions, methods and products of this invention, the relief imparted by the feverfew will be administered to the affected organs and systems of the body much more quickly than is possible through the prior art gastrointestinal system administration, and therefore migraine headaches and the discomforts of internal spasmodic cramping will be quickly and effectively alleviated.

We have discovered that by administering feverfew in the form of a nasal spray composed of an aqueous-based liquid and in which a small concentration of feverfew is dispersed or dissolved, the feverfew can be expeditiously administered without undue irritation of the nasal mucous membranes and acts rapidly and therapeutically to provide mucous membrane moisturization relief of migraine headaches and provides an antispasmodic effect resulting in relief of menstrual cramping and in aid to digestion. The effect is enhanced when the aqueous medium contains a portion of nanoclustered resonant water, particularly when the aqueous medium is also saline.

In broad definitions of the various aspects of the present invention, it includes a composition comprising an aqueous medium having incorporated therein a quantity of feverfew sufficient to provide at least a therapeutic moisturizing effect on nasal mucous membranes of a human user; a composition wherein the quantity of feverfew is sufficient to have a therapeutic effect of relief of migraine headache suffered by a human user; or a composition wherein the quantity of feverfew is sufficient to have a therapeutic antispasmodic effect on internal organs of a human user, such as the gastrointestinal system and the female reproductive system.

Similarly, other broad definitions of the various aspects of the present invention include a nasal spray comprising an aqueous medium having incorporated therein a quantity of feverfew sufficient to provide at least a therapeutic moisturizing effect on nasal mucous membranes of a human user; a nasal spray wherein the quantity of feverfew is sufficient to have a therapeutic effect of relief of migraine headache suffered by a human user; or a nasal spray wherein the quantity of feverfew is sufficient to have a therapeutic antispasmodic effect on internal organs of a human user, such as the gastrointestinal system and the female reproductive system.

In yet other broad definitions, the various aspects of the present invention include a composition comprising an aqueous medium having incorporated therein a quantity of parthenolide sufficient to provide at least a therapeutic moisturizing effect on nasal mucous membranes of a human user; a composition as wherein said quantity of parthenolide is sufficient to have a therapeutic effect of relief of migraine headache suffered by a human user; or a composition wherein said quantity of parthenolide is sufficient to have a therapeutic antispasmodic effect on internal organs of a human user, such as the gastrointestinal system and the female reproductive system.

Further broad definitions of the various aspects of the present invention include a method of relieving the physical effects of nasal dryness or irritation in a human by administration into a nasal cavity of the human a spray composition comprising an aqueous medium having incorporated therein a quantity of feverfew sufficient to provide at least a therapeutic moisturizing effect on nasal mucous membranes within the nasal cavity; a method of relieving the physical effects of migraine headache in a human by administration into a nasal cavity of the human a spray composition comprising an aqueous medium having incorporated therein a quantity of feverfew sufficient to have a therapeutic effect of relief of migraine headache suffered by the human; or a method of providing an antispasmodic effect to internal organs in a human by administration into a nasal cavity of the human a spray composition comprising an aqueous medium having incorporated therein a quantity of feverfew sufficient to have an antispasmodic therapeutic effect on said organs and thereby serving as a digestive aid for the human or providing relief of cramping or related spasm-associated effects suffered by the human.

The therapeutic effects of the present invention's compositions and methods can be enhanced by incorporation into the aqueous medium of a quantity of "clustered water," i.e., non-clustered resonant water. The medium may be saline and may also include vitamins, vitamin derivatives, surfactants, wetting agents, preservatives and emulsifiers.

DETAILED DESCRIPTION AND PREFERRED EMBODIMENTS

The crux of the present invention is our discovery that feverfew can be administered as a nasal spray and thus acts as an effective therapeutic agent without undesirable side effects and in a form palatable and tolerable to users. The nasal spray is in the form of a dilute aqueous solution or suspension of finely divided pieces of feverfew leaf.

Nasal administration of feverfew has never previously been described nor, to our knowledge, even considered as potentially effective. All administration of feverfew in the past, stretching back many years, has been for oral administration and delivery through the gastrointestinal tract, with strong emphasis that residence in the oral cavity must be minimal and must be tempered or buffered in some manner to counteract the known irritant and ulcerative properties of feverfew. Indeed, the modern incorporation of feverfew into pills or capsules which pass intact through the oral cavity and reach the gastrointestinal system without any release of feverfew represents complete confinement of feverfew for delivery through the gastrointestinal tract.

We have discovered, however, that the unique nasal spray administration method described herein is surprisingly effective in providing rapid assimilation and resulting therapeutic effect of the feverfew, by delivery through the nasal mucous membranes into the central nervous system.

Feverfew is an herb of the Compositae family. It has been known and described for many years by various herbalists, and is commonly used for decorative purposes because of its attractive leaves and flowers. There are several subspecies of feverfew, including golden feverfew, double feverfew, and american feverfew. As is further disclosed herein, feverfew has also been known or believed to have certain therapeutic effects on humans.

In the present invention, feverfew is provided by either by picking fresh leaves and allowing them to dry to a stage where they can be finely ground or otherwise comminuted, or by obtaining previously dried leaves, preferable already ground to the desired size. The dried leaf particles are dispersed or dissolved in an aqueous media, which may be pure water or water with various emulsifying agents, surfactants or other feverfew-compatible additives in it. The ground particle size for effective dissolution or dispersion is on the order of approximately 0.1–20 $\mu$m, more preferably 0.2–10 $\mu$m, and most preferable on the order of about 0.2–5 $\mu$m. Incorporation of the feverfew into the aqueous carrier may be aided by first dispersing the feverfew as a 4% concentration in a lactone solution. When thoroughly mixed and dispersed and/or dissolved, the feverfew will commonly be present at a concentration level in the aqueous carrier on the order of 0.001–2.0%, more preferably 0.01–0.35%, with a particularly preferred concentration on the order of about 0.10%. (All percentages herein are by weight unless otherwise noted.)

In preferred embodiments, the nasal spray composition will also have a small amount of nanoclustered resonant water present. This may conveniently be provided in the form of a clustered water buffering system which includes a borate buffer. The presence of the clustered water borate buffering system serves to enhance the therapeutic effects of the feverfew. It also is believed to stimulate the membrane cells and enhance the moisturizing effect of the aqueous medium on the nasal membranes. In the buffering system, the clustered water is formulated using a magnetic resonance process of the type described by Lorenzen. The clustered water remains chemically identical with the unprocessed water in the aqueous carrier, but when exposed to biological molecules, i.e., those making up the user's nasal system and nasal mucous membranes, the clusters form complexes that are believed to take on a structural and electronic signature of biomolecules and thus enhance the biological effectiveness of the nasal spray and of the therapeutic delivery of the feverfew.

Specifically, the clustered water is formed by using a novel process which is the subject of a co-pending patent application in the name of co-inventor Lorenzen. In this process highly distilled water is exposed to fluctuations in temperature ranging from −6° C. to 110° C. and electromagnetic fields ranging in power density in the range of 0.7–28 Tesla while being pumped through a ceramic coated baffle for a period of up to 24 hours. As no ceramic materials are transferred to the water during this process, the resulting solution meets or exceeds U.S. patent standards for "pure water." Further treatment with a tunable diode laser (50 watt) is used to induce the formation of water molecules into pentagonal, hexagonal and/or heptagonal ring structures. When the solution has reached the minimum target ring density of about 23% it is blended with the other nasal spray ingredients. Conveniently it is in the form of a borate buffer, which is present in a concentration in the range of 0.01–1.0%, preferably 0.05–0.50%, and more preferably on the order of about 0.10%. The ring structures improve the solubility of the other ingredients and enhance the bioactivity and membrane transfer effects of the product.

As noted, various other materials may also advantageously be present in the nasal spray in appropriate quantities. It is preferred to make the solution mildly saline, by dissolving a small amount of sodium chloride in the aqueous medium. The salt concentration may be in the range of 0.1–2.0% and will preferably be on the order of about 0.65%.

Other materials such as surfactants, vitamins and vitamin derivatives, antihistamines, wetting agents, preservatives, moisturizers, emulsifiers, odorants and the like may also be present in conventional concentrations. There are numerous disclosures of suitable materials in the literature, along with descriptions of efficacious concentrations in aqueous media. Those skilled in the art will have no difficulty in determining suitable materials and concentrations for their known functions.

Delivery of the spray to the nasal cavity may be by any conventional spray technique or device. Spray administration containers for various types of nasal sprays have been known in the past and substantially all will be equally suitable for the present invention, considering of course that the materials from which the container is made must be compatible with the spray composition. The aqueous liquid medium containing the feverfew, clustered water and other appropriate ingredients will commonly be contained in a small bottle or similar container with a focused nozzle, from which it can be dispersed as a fine mist to be directed into each nostril. Using ambient air as the propelling agent, one can have the bottle made of a flexible plastic, so that merely squeezing the bottle's sides impels the spray out through the nozzle into the nasal cavity. Air is also the propelling agent for a pump sprayer, in which the user manipulates a small pump button which pumps air into the container and causes the liquid spray to be emitted on the return stroke. Alternatively, the bottle can be pressurized with a gas which is inert to the user and to the ingredients of the solution. The gas will be dissolved under pressure in the container or may be generated by dissolution or reaction of a solid material which forms the gas as a product of dissolution or as a reaction product. Typical gases which can be used include nitrogen, argon, and carbon dioxide.

It is contemplated that the user will spray two or three sprays in each nostril at each administration, with the administration being repeated on an as needed basis. The frequency of administration will be dependent on the nature of the usage. If administration is for relief of a current condition, such as a current migraine headache, initial relief effects can be expected within a few minutes of administration. If such does not occur, the user may administer a second dosage. Dosages may be repeated at intervals as the effect wears off, if the headache persists. The user will normally discontinue administration once the headache has subsided. Administration can be resumed at a subsequent time when another headache occurs. It is also contemplated that the nasal spray can be administered regularly in smaller doses and on a less frequent basis, to create a prophylactic effect intended to prevent the onset of migraine headaches, menstrual cramps, intestinal spasms, or the like, or to serve as a dietary aid. It is recommended that the spray not be used by pregnant women, as there may be a small possibility that the feverfew may stimulate the uterus. Delivery rates will usually be on the order of about 50–100 $\mu$l per spray.

The composition will be seen to be useful for a number of different kinds of therapeutic uses. At its most basic level, the nasal spray serves as a moisturizer for the nasal mucous membranes, providing a soothing and moistening effect which alleviates the effects of dryness, wind, dust and other irritants on the nasal membranes.

At another level, and preferred for the present invention, the compositions of the present invention administered through the nasal spray serve as rapid and efficient therapeutic agents for relief of migraine headaches. The manner in which the feverfew component serves to alleviate migraine headaches has been the subject of a number of studies. It is believed that the effect primarily rises from the presence of parthenolide in the feverfew leaf. When application of the feverfew through the nasal spray is terminated, the migraine headache may return unless the causal conditions have in the meantime changed or themselves terminated. However, since for most sufferers migraine headaches rarely continue for more than a few hours or at most a few days, limited use of the feverfew nasal spray of the present invention over the appropriate period will be highly effective in suppressing the pain and other undesirable effects of the migraine headache for a period sufficient for the migraine-causing conditions to be eliminated by the natural processes of the body.

In yet another embodiment the application of the nasal spray of the present invention can provide an antispasmodic effect to internal organs which are subject to spasm under various conditions. For instance, shortly prior to and during menstruation, many women suffer cramping related to spasmodic reactions of the female reproductive organs, which may be relieved by administration of the present nasal spray during this time. Similarly, spasmodic reactions of the gastrointestinal systems can impair digestive function and cause intestinal discomfort to many people. The nasal spray may be used to aid digestion by acting as an antispasmodic and thus calm the smooth muscles of the digestive tract. Administration after meals if discomfort is experienced may prove beneficial. Since limited time periods are normally involved in both instances, repeated use of the nasal spray of the present invention on an as-needed basis is not anticipated to cause any significant problems. Once the immediate cramping or discomfort subsides, the user will normally discontinue application of the spray. Its use can be resumed if the cramping or discomfort reoccurs at a later time.

The following composition is an example of a typical efficacious nasal spray composition of the present invention.

| Ingredient | Content |
|---|---|
| feverfew (4% lactone) | 0.10% |
| clustered water borate buffer | 0.10% |
| NaCl | 0.65% |
| ascorbic acid derivative[1] | 0.20% |
| polyoxyethylene (20) sorbitan monooleate[2] | 0.13% |
| goldenseal[3] | 0.05% |
| benzalkonium chloride | 0.03% |
| ethylenediamine tetraacetic acid | 0.025% |

-continued

| Ingredient | Content |
| --- | --- |
| water | Balance |

[1] "Ester C" esterified commercial product
[2] "Polysorbate 80" commercial product
[3] *Hydrastis canadensis*, of the Ranunculaceae family It will be evident that there are numerous embodiments of the present invention, which, while not expressly set forth above, are clearly within the scope and spirit of the present invention. The above description is therefore intended to be exemplary only, and the invention is to be limited solely by the appended claims.

We claim:

1. A composition for nasal administration to a human user comprising a sprayable aqueous medium having dispersed or dissolved therein feverfew dried leaf particles having a particle size on the order of 0.1–2.0 µm, said feverfew being present in a concentration on the order of 0.001–2.0% in said aqueous medium and effective when administered as a spray to said human user's nasal mucous membranes to provide to said human user a therapeutic effect selected from the group consisting of a moisturizing effect on nasal mucous membranes of said human user, relief of migraine headache suffered by said human user, and an antispasmodic effect on internal organs of said human user.

2. A composition as in claim 1 wherein said quantity of feverfew is effective to have a therapeutic effect of relief of migraine headache suffered by said human user.

3. A composition as in claim 1 wherein said quantity of feverfew is effective to have an antispasmodic therapeutic effect on internal organs of said human user.

4. A composition as in any of claims 1, 2 or 3 wherein said feverfew is present in a concentration in the range of 0.01% to 0.35%.

5. A composition as in claim 4 wherein said feverfew is present in said aqueous medium in a concentration in on the order of 0.10%.

6. A composition as in any one of claims 1, 2 or 3 wherein said aqueous medium comprises clustered water.

7. A composition as in claim 5 wherein said clustered water is present in the form of a borate buffer dispersed in said aqueous medium.

8. A composition as in claim 7 wherein said buffer is present in said aqueous medium in a concentration in the range of 0.01–1.0%.

9. A composition as in claim 8 wherein said buffer is present in said aqueous medium in a concentration in the range of 0.05–0.50%.

10. A composition as in claim 9 wherein said buffer is present in said aqueous medium in a concentration on the order of 0.10%.

11. A composition as in any one of claims 1, 2 or 3 wherein said aqueous liquid is saline.

12. A composition as in any one of claims 1, 2 or 3 further comprising a material selected from the group consisting of surfactants, vitamins, vitamin derivatives, wetting agents, preservatives and emulsifiers.

13. A composition as in any one of claims 1 or 3 wherein internal organs which are affected by said antispasmodic effect are the gastrointestinal organs or the female reproductive organs.

14. A nasal spray for nasal administration to a human user comprising a sprayable aqueous medium having dispersed or dissolved therein feverfew dried leaf particles having a particle size on the order of 0.1–2.0 µm, said feverfew being present in a concentration on the order of 0.001–2.0% in said aqueous medium and effective when administered as a spray to said human user's nasal mucous membranes to provide to said human user a therapeutic effect selected from the group consisting of a moisturizing effect on nasal mucous membranes of said human user, relief of migraine headache suffered by said human user, and an antispasmodic effect on internal organs of said human user.

15. A nasal spray as in claim 14 wherein said quantity of feverfew is effective to have a therapeutic effect of relief of migraine headache suffered by said human user.

16. A nasal spray as in claim 14 wherein said quantity of feverfew is effective to have an antispasmodic therapeutic effect on internal organs of said human user.

17. A nasal spray as in any of claims 14, 15 or 16 wherein said feverfew is present in a concentration in the range of 0.01% to 0.35%.

18. A nasal spray as in claim 17 wherein said feverfew is present in a concentration on the order of 0.10%.

19. A nasal spray as in any one of claims 14, 15 or 16 wherein said aqueous medium comprises clustered water.

20. A nasal spray as in claim 19 wherein said clustered water is present in the form of a borate buffer dispersed in said aqueous medium.

21. A nasal spray as in claim 20 wherein said buffer is present in said aqueous medium in a concentration in the range of 0.01–1.0%.

22. A nasal spray as in claim 21 wherein said buffer is present in said aqueous medium in a concentration in the range of 0.05–0.50%.

23. A nasal spray as in claim 22 wherein said buffer is present in said aqueous medium in a concentration on the order of 0.10%.

24. A nasal spray as in any one of claims 14, 15 or 16 wherein said aqueous liquid is saline.

25. A nasal spray as in any one of claims 14, 15 or 16 further comprising a material selected from the group consisting of surfactants, vitamins, vitamin derivatives, wetting agents, preservatives and emulsifiers.

26. A nasal spray as in any one of claims 14 or 16 wherein internal organs which are affected by said antispasmodic effect are the gastrointestinal organs or the female reproductive organs.

27. A composition comprising a sprayable aqueous medium having dispersed or dissolved therein parthenolide incorporated in feverfew dried leaf particles having a particle size on the order of 0.1–2.0 μm, said feverfew particles being present in a concentration on the order of 0.001–2.0% in said aqueous medium and effective when administered as a spray to said human user's nasal mucous membranes to provide to said human user a therapeutic effect selected from the group consisting of a moisturizing effect on nasal mucous membranes of said human user, relief of migraine headache suffered by said human user, and an antispasmodic effect on internal organs of said human user.

28. A composition as in claim 27 wherein said quantity of parthenolide is effective to have a therapeutic effect of relief of migraine headache suffered by a human user.

29. A composition as in claim 27 wherein said quantity of parthenolide is effective to have an antispasmodic therapeutic effect on internal organs of said human user.

30. A composition as in any of claims 27, 28 or 29 wherein said parthenolide is present in a concentration in the range of 0.01% to 0.35%.

31. A composition as in claim 30 wherein said parthenolide is present in said aqueous medium in a concentration in on the order of 0.10%.

32. A composition as in any one of claims 27, 28 or 29 wherein said aqueous medium comprises clustered water.

33. A composition as in claim 32 wherein said clustered water is present in the form of a borate buffer dispersed in said aqueous medium.

34. A composition as in claim 33 wherein said buffer is present in said aqueous medium in a concentration in the range of 0.01% to 1.0%.

35. A composition as in claim 34 wherein said buffer is present in a concentration in the range of 0.05% to 0.50%.

36. A composition as in claim 35 wherein said buffer is present in a concentration on the order of 0.10%.

37. A composition as in any one of claims 27, 28 or 29 wherein said aqueous liquid is saline.

38. A composition as in any one of claims 27, 28 or 29 further comprising a material selected from the group consisting of surfactants, vitamins, vitamin derivatives, wetting agents, preservatives and emulsifiers.

39. A composition as in any one of claims 27 or 29 wherein internal organs which are affected by said antispasmodic effect are the gastrointestinal organs or the female reproductive organs.

* * * * *